United States Patent
Zhang et al.

(10) Patent No.: US 8,783,101 B2
(45) Date of Patent: Jul. 22, 2014

(54) RAPID RESPONSE RELATIVE HUMIDITY SENSOR USING ANODIC ALUMINUM OXIDE FILM

(75) Inventors: Chun Zhang, Hong Kong (HK); Jianying Miao, Hong Kong (HK); Ning Wang, Hong Kong (HK)

(73) Assignee: Nano and Advanced Materials Institute Limited, Hong Kong (HK)

( * ) Notice: Subject to any disclaimer, the term of this patent is extended or adjusted under 35 U.S.C. 154(b) by 77 days.

(21) Appl. No.: 13/380,053

(22) PCT Filed: Dec. 22, 2010

(86) PCT No.: PCT/CN2010/080145
§ 371 (c)(1),
(2), (4) Date: Dec. 22, 2011

(87) PCT Pub. No.: WO2011/076124
PCT Pub. Date: Jun. 30, 2011

(65) Prior Publication Data
US 2012/0247203 A1    Oct. 4, 2012

Related U.S. Application Data (60) Provisional application No. 61/282,139, filed on Dec. 22, 2009.

(51) Int. Cl.
*G01N 19/10* (2006.01)
*G01N 27/22* (2006.01)

(52) U.S. Cl.
CPC ................................ *G01N 27/223* (2013.01)
USPC .............. 73/335.04; 73/335.02; 73/335.05; 73/29.01; 73/29.02; 73/29.05; 422/664; 422/689

(58) Field of Classification Search
CPC ....... G01N 19/10; G01N 33/18; G01R 27/22; G01R 27/26
USPC .......... 73/31.05, 31.06, 335.04, 29.01–29.05, 73/335.02–335.05; 205/201; 361/280, 361/281, 286, 303; 324/664, 689
See application file for complete search history.

(56) References Cited

U.S. PATENT DOCUMENTS 3,523,244 A * 8/1970 Chleck et al. ................. 324/689
4,217,623 A * 8/1980 Nishino et al. ............... 361/280

(Continued)

FOREIGN PATENT DOCUMENTS

CN          86102535 A        5/1988
JP          49070674 A        7/1974

*Primary Examiner* — Hezron E Williams
*Assistant Examiner* — Hoang Nguyen
(74) *Attorney, Agent, or Firm* — Ella Cheong Hong Kong; Sam T. Yip (57) ABSTRACT

A rapid response relative humidity sensor based on nano-structured aluminum oxide thin film is disclosed. The main body of the sensor is an anodic aluminum oxide thin film of about 2-20 μm thick formed from an Al substrate which serves as one electrode. A porous metal layer of about 20-200 nm thick is formed over the anodic aluminum oxide thin film and functions as a second electrode. The alumina thin film contains nano-sized channels of about 10-100 nm in diameter, serving as a capacitive relative humidity sensor having high sensitivity and short response time. Thermal annealing at elevated temperature improves the linearity of the capacitance versus humidity curve, giving a full range humidity sensing range. Hysteresis and degradation are negligible for the humidity sensors.

11 Claims, 6 Drawing Sheets

(56) References Cited

U.S. PATENT DOCUMENTS

| | | | | |
|---|---|---|---|---|
| 4,393,434 A | * | 7/1983 | Imai et al. | 361/286 |
| 4,651,121 A | * | 3/1987 | Furubayashi et al. | 338/35 |
| 4,965,698 A | * | 10/1990 | Thoma et al. | 361/286 |
| 5,050,434 A | * | 9/1991 | Demisch | 73/335.04 |
| 5,177,662 A | * | 1/1993 | Thoma | 361/286 |
| 5,814,726 A | * | 9/1998 | Mitter | 73/335.04 |
| 7,032,448 B2 | * | 4/2006 | Hamamoto | 73/335.04 |
| 7,077,004 B2 | * | 7/2006 | Mitter | 73/335.04 |
| 2007/0210807 A1 | * | 9/2007 | Arisaka | 324/664 |
| 2011/0259099 A1 | * | 10/2011 | Hong et al. | 73/335.04 |

* cited by examiner

RAPID RESPONSE RELATIVE HUMIDITY SENSOR USING ANODIC ALUMINUM OXIDE FILM

FIELD OF THE INVENTION

The invention relates to anodic aluminum oxide thin film sensors, and, more particularly, to rapid response capacitive relative humidity sensors based on nano-structured aluminum oxide thin film material.

BACKGROUND

Humidity sensors are useful in many applications such as weather stations, air conditioning, home and office appliances, and industrial instruments. For electronic-type relative humidity sensors, polymer-based humidity sensors dominate the market, due to their low cost and mature manufacturing processes. However, for high performance humidity sensors semiconductor material-based and ceramic material-based sensors are often used.

An anodic porous aluminum oxide (AAO) film (Al foil anodized in an acid solution) is a known ceramic material for the fabrication of humidity sensors. The first humidity-sensitive anodized alumina layer on aluminum substrate was reported in 1953. The capacitance of such a structure was found to increase with relative humidity. Aluminum oxide-based humidity-sensitive materials attracted increased attention since 1978, when a regular honeycomb structure aluminum oxide material was developed. There have been intensive studies to develop high performance and reliable sensors based on such a novel nano-structured material.

Anodizing is a well-developed technique for producing protective AAO layers, for example, on aluminum for structure applications such as window frames. However, anodization techniques for protective applications were not directly applicable to creating AAO-based humidity sensors. The humidity response of an AAO thin film is highly dependent on the anodizing parameters. For example, prior humidity sensors have a capacitance versus humidity response that is often nonlinear, with a 'flat' response in low or high humidity; such sensors cannot operate in a full humidity range. The long-term stability of a humidity sensor is another major concern; prior AAO sensors degrade when exposed to high humidity. Proposals to resolve the problems of prior art humidity sensors depended on sophisticated structural designs and/or fabrication processes, resulting in unacceptable manufacturing costs for commercial production. Therefore, only limited progress has been made in forming absolute humidity sensors based on anodic aluminum oxide.

Thus there is a need in the art for cost-effective rapid response humidity sensors bases on anodic aluminum oxide which have a substantially linear capacitance versus humidity response and can measure a full range of humidity conditions.

SUMMARY OF THE PRESENT INVENTION

The present invention provides a simple, cost-effective, and reliable process in fabricating stable, rapid response, and full-range humidity sensors based on anodic aluminum oxide thin films. The anodic aluminum oxide films contain nano-sized channels having fully controllable pore diameter (from a few nanometers to a few hundred nanometers), pore depth, and pore density by tuning the anodizing conditions. With extensive surface area in such a porous structure, high humidity sensitivity and fast response can be achieved. Moreover, the anodic alumina thin films are thermally and chemically stable, forming stable humidity sensors usable even in harsh environments.

DETAILED DESCRIPTION

Figure 1:
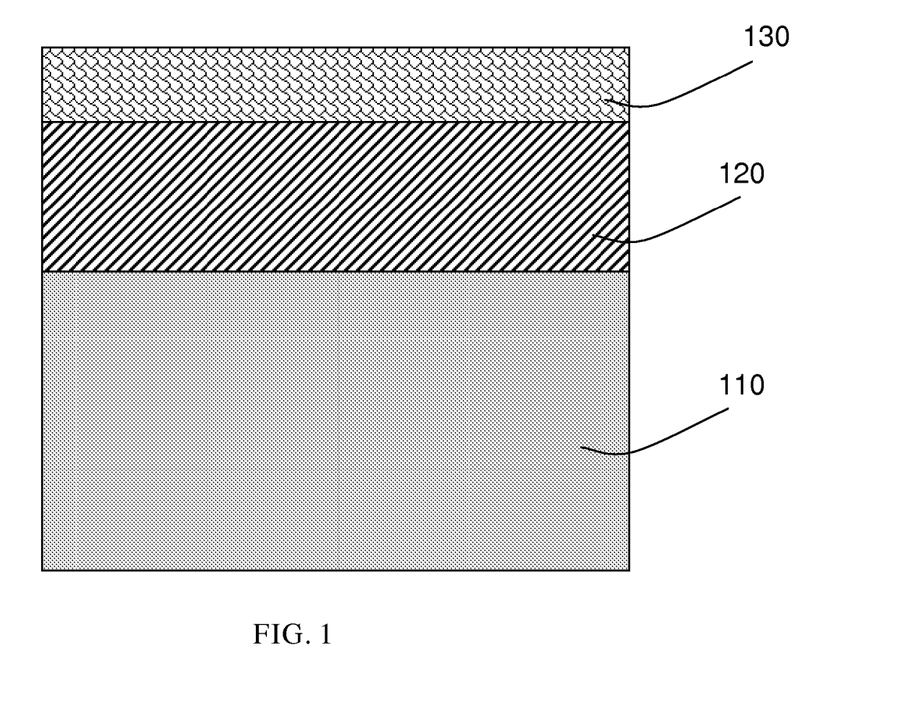
FIG. 1: Schematic side view of a capacitive humidity sensor based on an anodic aluminum oxide thin film.

Turning to the drawings in detail, embodiments of the present invention show capacitive humidity sensors using anodic aluminum oxide thin films. FIG. 1 is a schematic diagram of a sensor. The various components are not shown to scale relative to each other.

The main body of the sensor is an anodic aluminum oxide (AAO) thin film 120 having a thickness of about 2-20 μm. AAO film 120 is sandwiched between a top metal layer electrode 130 having a thickness of about 20-200 nm, and an Al substrate 110 as the other electrode. The AAO thin film contains nano-sized channels of about 10-100 nm in diameter. In operation, water vapor is adsorbed onto the AAO film channel surfaces, changing the capacitance of the AAO film. Because the nano-structured films can be carefully controlled as to channel size and thickness, rapid response humidity sensors result due to the high surface area provided by the nano-sized channels.

Figure 2:
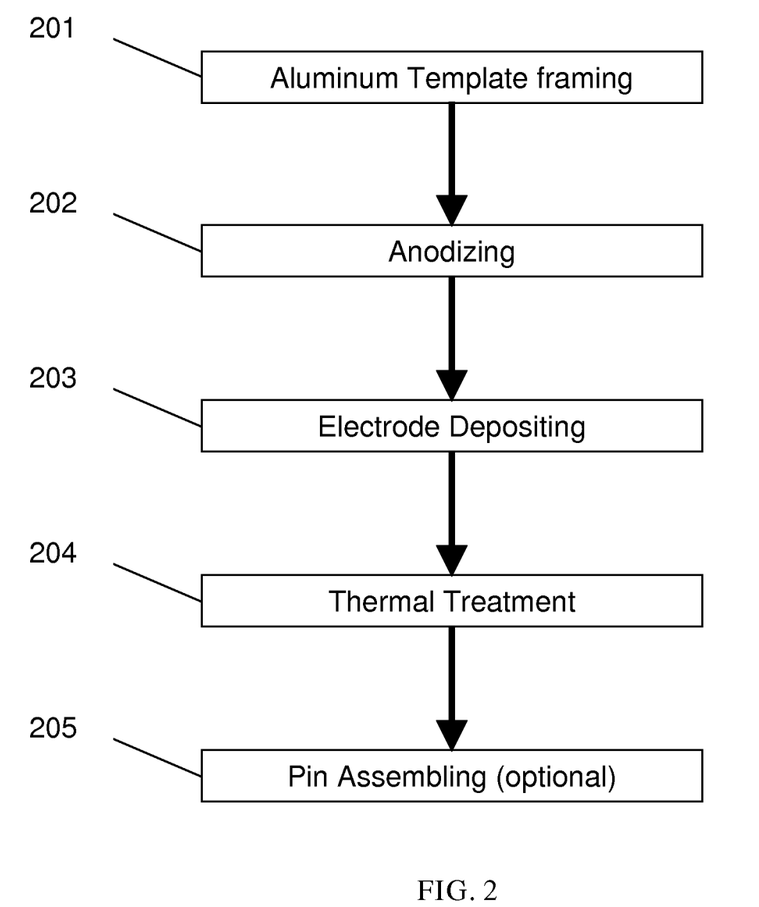
FIG. 2: Flowchart of a fabrication process for a capacitive humidity sensor based on an anodic aluminum oxide thin film.

The fabrication of the humidity sensors of the present invention is outlined below with reference to the flow chart of FIG. 2. The process conditions discussed below are exemplary conditions for forming the particular dimensions of FIG. 2.

In step 201, the starting material is an aluminum sheet with a thickness of 0.6 mm. To create a suitable shape for a capacitive humidity sensor, the aluminum sheet is stamped into a shape such as the one shown in FIG. 3.

Figure 4:
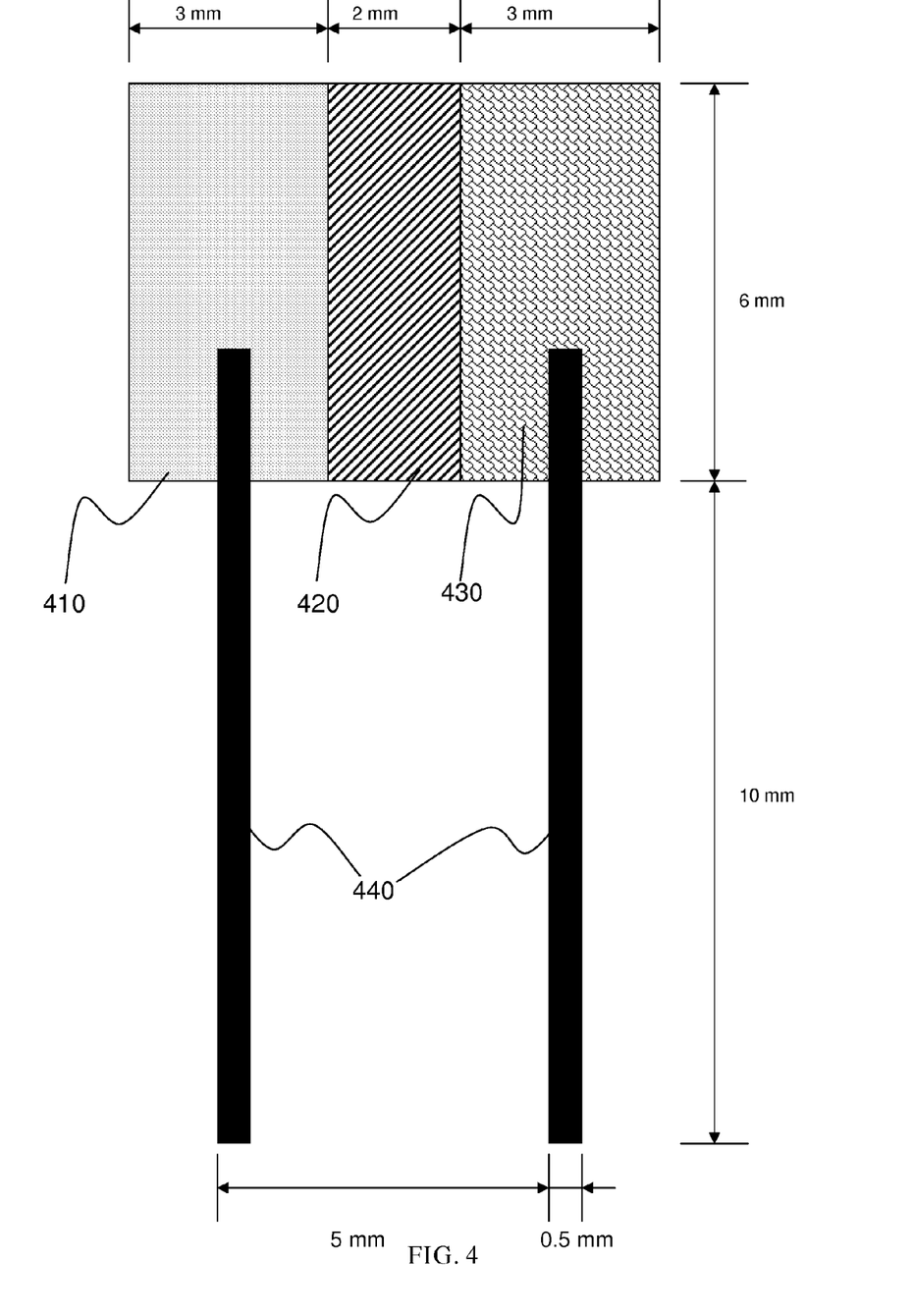
FIG. 4: A humidity sensor according to a further embodiment of the present invention.

Alternatively, in step 201, the starting material is an aluminum sheet with a thickness of 0.8 mm and is stamped into the shape shown in FIG. 4.

The framed aluminum templates of step 201 are anodized in step 202. In one exemplary embodiment, films having channels of 40 nm diameter and a thickness of 15 μm are formed. For a film of these dimensions, anodization was carried out in 0.3M oxalic acid at 20° C. The current density is maintained at 4 A/dm$^2$, and the voltage was maintained at about 30V. For the 15 μm film, 4 hour anodization time is used. After the anodization, the sensor plates are rinsed in water to remove the acid residuals, and then dried under ambient at elevated temperature.

For the making of humidity sensor, the range of channel diameter is preferably from 10 to 100 nm, and the thickness from 2-20 μm. This can be tuned by varying the acid content and concentration, and by adjusting the current density and operation temperature and time. Typically, higher voltages result in larger channel diameters while the thickness of the anodized alumina is generally determined by anodizing time. Anodizing techniques are often grouped into potentiostatic and galvanostatic anodization techniques. In potentiostatic anodization, more uniform channel sizes can be achieved through the entire anodized layer. However, the current density and the growth rate of the aluminum oxide decrease with time. In galvanostatic anodization, the aluminum oxide grows at a fairly uniform rate although the voltage and pore diameter increase over the period of anodization. A combination of these techniques can be used, sequentially, to achieve a selected morphology and commercially acceptable process time.

Figure 3:
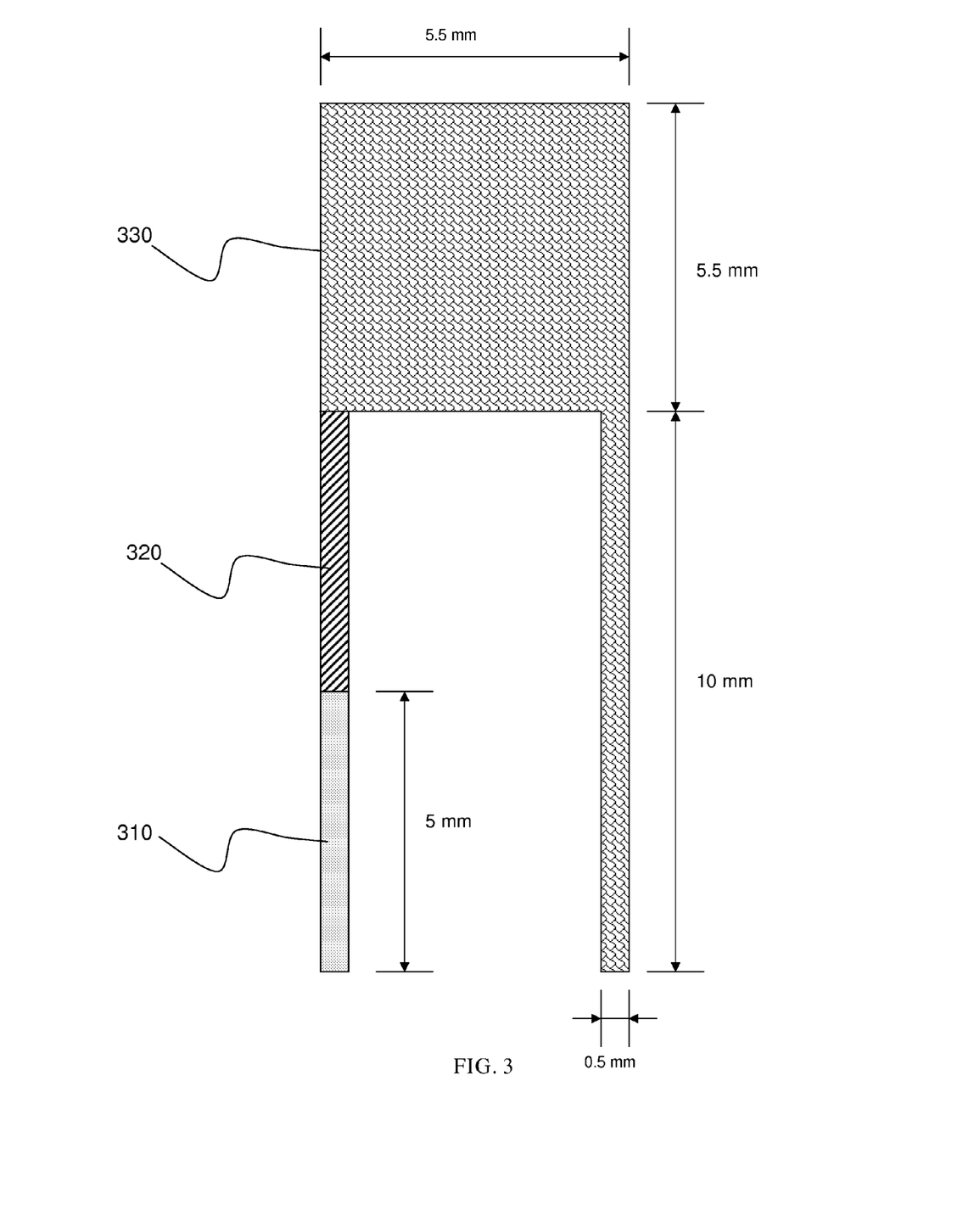
FIG. 3: A humidity sensor according to one embodiment of the invention.

FIG. 3 schematically depicts a side view of a humidity sensor structure in which 310 is an unanodized Al substrate, 320 is anodized aluminum oxide on top of Al substrate 310, and 330 is a permeable metal layer formed over the AAO and Al substrate. The permeable metal layer may be a porous metal layer, for example, of aluminum that coats the tops of the channel edges, permitting water vapor to permeate the AAO layer.

FIG. 4 schematically depicts a side view of an alternative humidity sensor structure. 410 is an unanodized Al substrate, 420 is AAO formed on top of Al substrate 410, 430 is a permeable metal layer on top of AAO layer 420 and Al substrate 410, and 440 are solderable electrode pins attached to the sensor through spring contacts or conductive glue.

To fabricate the humidity sensors of FIGS. 3 and 4, only regions 320 and 330 in FIG. 3 and regions 420 and 430 require an anodized layer. Regions 310 and 410 must be conductive to function as an electrode. This can be achieved by different approaches:
  i) Shield regions 310 and 410 during anodization (e.g., a protective coating) or refrain from contacting areas 310 and 410 with the acid solution during anodization;
  ii) Anodize the entire template structure (that is, the entire shape of FIGS. 3 and 4 without electrodes 440) followed by removal of the anodized layer from regions 310 and 410; or
  iii) Anodize the entire template and deposit a metal layer on the regions 310 and 410 and create a contact between the deposited metal layer and the aluminum substrate.

The permeable metal layers 330 and 430 are preferably formed by deposition on a surface of the AAO layer in those regions. The thickness of the conductive layer is preferably from 20-200 nm. The conductive layer is preferably of the same material, for example, Au or Al. The deposit can be made, for example, by way of sputtering coating. As discussed above, because the AAO layer is itself porous, the deposited metal layer will cover the edges of the porous channels, resulting in a metal layer permeable to moisture.

Because only regions 330 and 430 in FIG. 3 and FIG. 4 are covered with the conductive layer, areas 310 and 320 and areas 410 and 420 can be shielded or masked during deposition of the conductive layer.

To achieve a more linear response for the humidity sensors of the present invention, the structures of FIGS. 3 and 4 are thermally treated following the metal deposition process. Exemplary thermal treatment conditions are set forth below:
  i) The structure is annealed at a temperature of 85° C. for 5-50 hours at 90% relative humidity; or
  ii) The structure is annealed at a temperature of 90° C. for 5-50 hours in dry air; or
  iii) The structure is immersed in boiling water at a temperature of 100° C. for 10-100 minutes.

For the embodiment of FIG. 3, the completed sensor uses regions 310 (the bare Al pin) and 330 (the metal-on-AAO-on-Al pin) as the two electrodes. The structure of FIG. 3 can be directly plugged into a circuit as a humidity-sensitive capacitor.

For the embodiment of FIG. 4, two external pins 440 are assembled to the formed structure as electrodes for the humidity sensor. The two pins are attached to the structure through spring contacts or conductive glue, with one pin in contact with region 410 (the bare Al area) and the other pin in contact with region 430 (the metal-on-AAO-on-Al area) serving as two electrodes. The two pins are optionally made of solderable metals or metal alloys, for example, brass and tin. The resulting device can be plugged or soldered into a circuit as a humidity-sensitive capacitor.

In the exemplary process of making an AAO-based relative humidity sensor (FIG. 2), the main processes are: aluminum template framing (201), anodizing (202), electrode depositing (203), thermal treatment (204), and pin assembling (205, optional).

The simple template designs in FIGS. 3 and 4 result in high yield-rate and low-manufacturing-costs production for the final humidity sensors. For mass production, the template design is configured to the equipment for anodizing, electrode depositing, and thermal treatment for a high-efficiency and less-demanding process.

Figure 5:
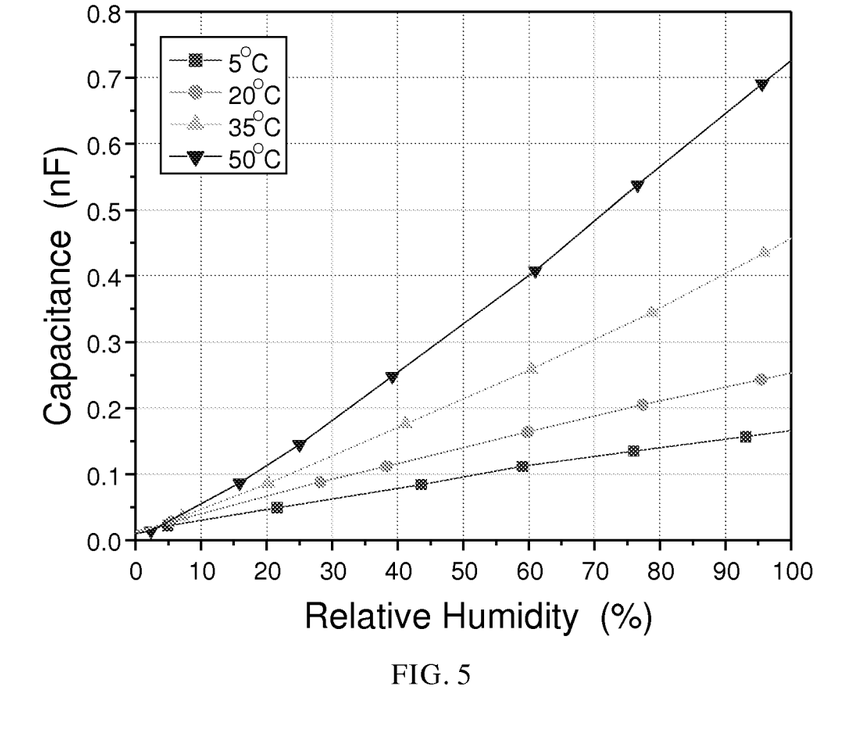
FIG. 5: Capacitance versus humidity curves at temperatures of 5° C., 20° C., 35° C., 50° C. for an AAO-based humidity sensor of the present invention.

The present invention uses anodic alumina thin films as the sensing elements. The anodic alumina thin film contains nano-sized channels with fully controllable pore diameter, depth, and density by tuning the anodizing conditions. For example, FIG. 5 is obtained from a sensor made with nano-sized channels at approximately 40 nm in pore diameter and approximately 15 μm in depth. The capacitance versus humidity curves of FIG. 5 are measured at 5° C., 20° C., 35° C., and 50° C., respectively. As a result of the processes of the present invention, the curves exhibit close-to-linear responses in a full humidity range from 0-100% relative humidity. The typical capacitance at 20° C. and 60% relative humidity is 165 pF.

The sensitivity of the sensors of the present invention can be improved by increasing the effective sensing area or by reducing the thickness of the AAO film. The response time is mainly determined by the pore size of the nano-channels. For example, for a sensor made with nano-sized channels of approximately 40 nm pore diameter, the response time is <1 s in the humidity range of 30-90% relative humidity. For another sensor made with nano-sized channels at <10 nm in pore diameter, the response time is ~6 s in the humidity range of 30-90% relative humidity.

Figure 6A:
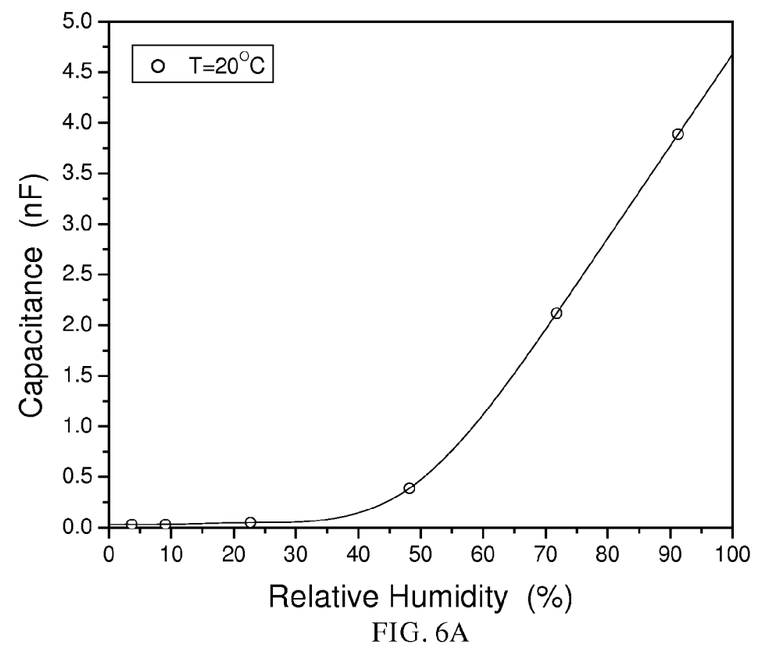
FIGS. 6A and 6B: Capacitance versus humidity curves of an AAO-based humidity sensor before and after thermal treatment measured at 20° C.
Figure 6B:
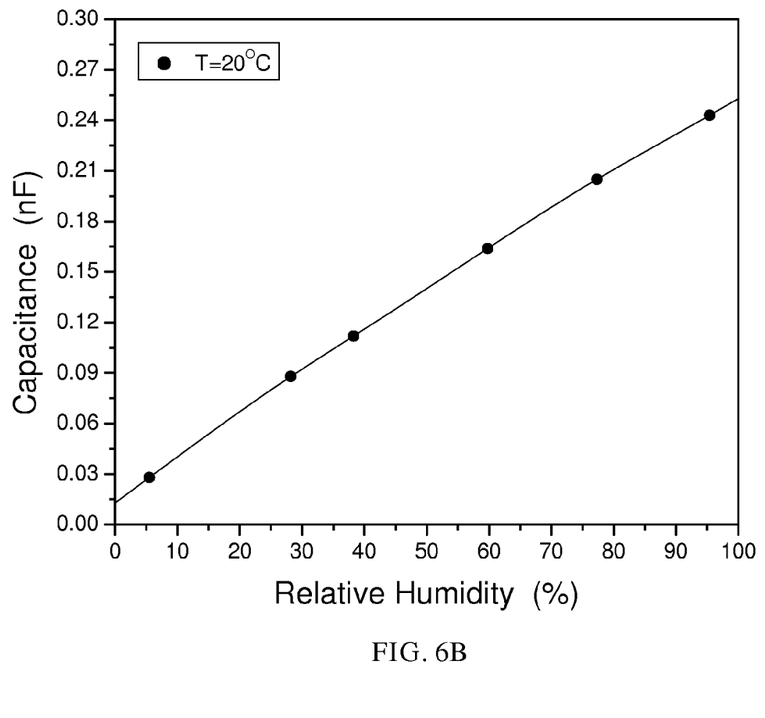

Thermal treatment improves the performance of the sensor. As shown in FIG. 6A, a sensor made before thermal treatment exhibits a non-linear response. The capacitance reading is almost identical in the flat relative humidity region that is lower than 30% relative humidity. Therefore such a device has a humidity sensing range limited to about 30-100% relative humidity. For the same sensor made after thermal treatment as shown in FIG. 6B, the capacitance response becomes lower. However, the capacitance versus humidity curve exhibits close-to-linear response in the full humidity range of from 0-100% relative humidity. Further, sensors made according to the present invention exhibit negligible hysteresis.

Thermal treatment also improves the stability of the sensor. A sensor after thermal treatment maintains the same capacitance to humidity response while it is operating under normal operation at temperatures below 50° C. and humidity below 90% relative humidity for approximately one year. A sensor made without thermal treatment is less stable and deteriorates rapidly under high humidity conditions.

Industrial Applicability

Compared to previous AAO-humidity sensors, the sensors made according to the present invention present the following features in one unit: (1) competitive sensitivity and response time, (2) operation in a full humidity range 0-100% relative humidity, (3) comparatively long-term stability, and (4) simple fabrication process at low cost. It is suitable for mass production for various applications such as in air conditioning systems, humidifiers and dehumidifiers, industrial processes requiring precise humidity control such as annealing treatments, and in measuring ambient humidity for weather forecasts.

The invention claimed is:

1. A capacitive humidity sensor having a substantially linear response and capable of detecting relative humidity in a full range of 0 to 100% relative humidity, the humidity sensor comprising:
   an aluminum substrate forming one electrode of the capacitive humidity sensor;
   an anodic aluminum oxide thin film formed from at least a portion of the aluminum substrate and having a thickness of 2-20 μm formed on a portion of the aluminum substrate, the anodic aluminum oxide film having channels with a channel diameter from 10 nm to 100 nm configured to adsorb water vapor from an ambient environment; and
   a porous metal layer formed on a portion of the anodic aluminum oxide film formed on the aluminum substrate, the porous metal layer forming a second electrode of the capacitive humidity sensor, the aluminum substrate, anodic aluminum oxide thin film and porous metal layer having undergone heat treatment to produce a substantially linear humidity versus capacitance sensor response,
   wherein said heat treatment is selected from one of the following conditions:
   a) annealing at a temperature of 85° C. for 5-50 hours at 90% relative humidity;
   b) annealing at a temperature of 90° C. for 5-50 hours in dry air; or
   c) immersion in boiling water at a temperature of 100° C. for 10-100 minutes; and
   wherein a response time of said capacitive humidity sensor is less than 6 seconds when the channel diameter is larger than 10 nm.

2. The capacitive humidity sensor according to claim 1, wherein the response time is less than 1 second when the channel diameter is larger than 40 nm.

3. The capacitive humidity sensor according to claim 1 further comprising metal electrode pins extending from the aluminum substrate and the porous metal layer.

4. The capacitive humidity sensor according to claim 1 wherein the aluminum substrate is plate-shaped with two integrally formed electrode legs extending therefrom, one of the electrode legs comprising unanodized aluminum and the other electrode leg comprising anodized aluminum with the porous metal layer formed thereon.

5. The capacitive humidity sensor according to claim 1, wherein the aluminum substrate is plate shaped with an attached electrode leg extending from an unanodized portion of the aluminum substrate and another attached electrode leg extending from the anodized portion of the aluminum substrate having the porous metal layer formed thereon.

6. A process for fabricating the capacitive humidity sensor of claim 1 comprising:
   forming an aluminum template from an aluminum substrate;
   anodizing at least a portion of the aluminum template;
   depositing a porous metal film on at least a portion of the anodized aluminum template; and
   thermally treating the resulting multilayer structure to create a substantially linear humidity versus capacitance response humidity sensor.

7. A method according to claim 6, wherein anodizing is carried out in oxalic acid, or sulfuric acid, or phosphoric acid, or nitric acid, or a mixture thereof.

8. A method according to claim 6, the porous metal film is aluminum, copper, gold, platinum, palladium, or nichrome.

9. A method according to claim 6, wherein the thermal treatment comprises annealing at a temperature of 85° C. for 5-50 hours at 90% relative humidity.

10. A method according to claim 6, wherein the thermal treatment comprises annealing at a temperature of 90° C. for 5-50 hours in dry air.

11. A method according to claim 6, wherein the thermal treatment comprises immersion in boiling water at a temperature of 100° C. for 10-100 minutes.

* * * * *